(12) United States Patent
Pouchoulin

(10) Patent No.: US 12,364,796 B2
(45) Date of Patent: *Jul. 22, 2025

(54) APPARATUS FOR EXTRACORPOREAL TREATMENT OF BLOOD

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/873,561

(22) Filed: Jul. 26, 2022

(65) Prior Publication Data

US 2022/0355008 A1 Nov. 10, 2022

Related U.S. Application Data

(63) Continuation of application No. 16/321,115, filed as application No. PCT/EP2017/068983 on Jul. 27, 2017, now Pat. No. 11,419,968.

(30) Foreign Application Priority Data

Jul. 28, 2016 (EP) ..................................... 16181664

(51) Int. Cl.
*A61M 1/16* (2006.01)
*A61M 1/34* (2006.01)
(Continued)

(52) U.S. Cl.
CPC ........ *A61M 1/1694* (2013.01); *A61M 1/1629* (2014.02); *A61M 1/1658* (2013.01);
(Continued)

(58) Field of Classification Search
CPC .............. A61M 1/1629; A61M 1/1658; A61M 1/1664; A61M 1/1694; A61M 1/34;
(Continued)

(56) References Cited

U.S. PATENT DOCUMENTS 3,878,095 A * 4/1975 Frasier ................ A61M 1/1668
210/321.71
4,079,007 A * 3/1978 Hutchisson ......... A61M 1/1605
210/321.71
(Continued)

FOREIGN PATENT DOCUMENTS

DE 29518797 9/1996
EP 2995329 3/2016

OTHER PUBLICATIONS

International Search Report and Written Opinion for International Application No. PCT/EP2017/068983; mailed Oct. 11, 2017; (13 pages).

*Primary Examiner* — Dirk R Bass
(74) *Attorney, Agent, or Firm* — K&L Gates LLP

(57) ABSTRACT

An extracorporeal blood treatment apparatus comprises a blood treatment device (2), an extracorporeal blood circuit, a blood pump (8) configured to be coupled to a blood withdrawal line (6) of the extracorporeal blood circuit. A closed fluid line (10) is connected to an inlet port (4*a*) and to an outlet port (4*b*) of a fluid chamber (4) of the blood treatment device (2), wherein the closed fluid line (10) together with the fluid chamber (4) forms a recirculation loop. An evacuation line (15) departs from the closed fluid line (10). A warming device (13) and a recirculation pump (17) are coupled or configured to be coupled to the closed fluid line (10). At least one temperature sensor (22) is operative on the extracorporeal blood circuit and it is configured to sense a blood temperature (Tb). A control unit (25), connected to the warming device (13), to the recirculation pump (17) and to the temperature sensor (22), is configured to execute the following procedure: receiving from the temperature sensor (22) at least a signal correlated to the blood temperature (Tb); adjusting the blood tempera- (Continued)

ture (Tb) by controlling at least one of the warming device (13) and the recirculation pump (17).

20 Claims, 6 Drawing Sheets

(51) Int. Cl.
*A61M 1/36* (2006.01)
*A61M 1/14* (2006.01)

(52) U.S. Cl.
CPC ............ *A61M 1/1664* (2014.02); *A61M 1/34* (2013.01); *A61M 1/3496* (2013.01); *A61M 1/3612* (2014.02); *A61M 1/3629* (2014.02); *A61M 1/153* (2022.05); *A61M 2205/3331* (2013.01); *A61M 2205/3368* (2013.01); *A61M 2205/36* (2013.01); *A61M 2230/50* (2013.01)

(58) Field of Classification Search
CPC .............. A61M 1/3496; A61M 1/3612; A61M 1/3629; A61M 2205/3331; A61M 2205/3368; A61M 2205/36; A61M 2230/50
See application file for complete search history.

(56) References Cited

U.S. PATENT DOCUMENTS

| | | |
|---|---|---|
| 4,894,164 A | 1/1990 | Polaschegg |
| 5,247,434 A | 9/1993 | Peterson et al. |
| 2009/0120864 A1* | 5/2009 | Fulkerson ............... A61M 1/16 210/321.71 |

* cited by examiner

FIG.5

The desired blood temperature Tbp at the outlet 3a of the blood chamber 3 is set The fluid flow rate Qr in the recirculation loop 10 is fixed to a preset fluid flow rate Qrp A maximum fluid temperature Tfmax at the outlet of the warming device 13 is set

↓

Blood treatment is started

↓

The control unit 25:

receives from the blood temperature sensor 22 a signal correlated to the blood temperature Tb at the outlet 3b of the blood chamber 3 receives from the fluid temperature sensor 24 a signal correlated to the fluid temperature Tf at the outlet of the warming device 13

↓

The control unit 25:

maintains a fixed rotational speed of the recirculation pump 17 corresponding to the preset fluid flow rate Qrp regulates the power of the fluid warming device 13 to bring and keep the measured blood temperature Tb equal to the preset blood temperature Tbp controls the power of the fluid warming device 13 so that the fluid temperature Tf does not exceed the maximum fluid temperature Tfmax

APPARATUS FOR EXTRACORPOREAL TREATMENT OF BLOOD

PRIORITY CLAIM

This application is a continuation of U.S. patent application Ser. No. 16/321,115, filed Jan. 28, 2019, entitled Apparatus for Extracorporeal Treatment of Blood, now U.S. Pat. No. 11,419,968, which is a National Stage of International Application No. PCT/EP2017/068983, filed Jul. 27, 2017, which claims priority to European Patent Application No. 16181664.0 filed on Jul. 28, 2016, the entire contents of each of which are incorporated herein by reference and relied upon.

DESCRIPTION

Field of the Invention

The present invention relates to an apparatus for extracorporeal treatment of blood. The extracorporeal blood treatment apparatus according to the invention is combined with, or comprises, a blood-warming device. The blood-warming device may be part of the extracorporeal blood treatment apparatus or may be a separate device which is in communication with the extracorporeal blood treatment apparatus. The invention also concerns a method of controlling blood warming in an extracorporeal blood circuit of an extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and/or to add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemo-filter) where the blood is allowed to flow past a semi-permeable membrane. The semi-permeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable fluid is removed from the blood by convection across the membrane into the secondary chamber. In a hemofiltration (HF) treatment, the blood flows past the semipermeable membrane as in UF (where waste and undesirable fluid are removed) and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semi-permeable membrane into the secondary fluid by diffusion and desirable matter from the secondary fluid crosses the membrane into the blood. In a hemodiafiltration (HDF) treatment, blood and secondary fluid exchange matter as in HD, and, in addition, matter is added to the blood, typically by dispensing a fluid into the treated blood (infusion) either before and/or after it passes through the treatment unit and before its return to the patient as in HF.

During extracorporeal blood treatment therapies, the patient may lose significant amount of heat due to infusion fluids having lower temperature than blood, due to fluid exchange across the membrane of the treatment unit, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic HD or HDF, and in the case of low volume but continuous therapies like continuous renal replacement therapy (CRRT) (used in e.g. acute HD). Furthermore, the risk of hypothermia is even more problematic in case of treatments applied to low body weight patients, such as children. Blood cooling due to fluid exchange (treatment and/or infusion fluids) is usually more important than heat losses to atmosphere in the complete extracorporeal blood circuit. In order to prevent hypothermia during extracorporeal blood treatment several solutions have been developed in the past.

Background

In accordance with a known solution and in order to solve the above problems, blood warmers acting on the blood return line and capable of directly warming blood have been used. Blood warming introduces at least one additional component in the blood circuit, with the associated risks related to clotting and/or haemolysis.

In accordance with other solutions, patient's blood cooling is prevented by warming each of the infusion fluids prior to their infusion in the blood circuit or dialyzer. These fluid warming systems have some drawbacks. When fluids of different compositions have to be used for the therapy, these systems become cumbersome due to the number of warming systems and associated disposable. Testing has evidenced strong limitations in the performance of current fluid warming systems when the fluid exchange rate becomes low (typically <2000 ml/h), with the impossibility to compensate for the heat losses to atmosphere of the blood circuit.

Some other documents disclose to heat the dialysate which in turn heats the blood.

Document EP2319551 discloses an apparatus for hemodialysis comprising a dialyzer, an ultrafilter and an external dialysate circuit which provides fresh dialysate to the ultrafilter and receives used dialysate from the internal dialysate circuit. The external dialysate circuit includes a dialysate pump, which pumps dialysate from a dialysate tank through a heater and/or the ultrafilter to the balancing circuit. The heater may be used to warm the dialysate to body temperature, and/or a temperature such that the blood in the blood flow circuit is heated by the dialysate, and the blood returning to the patient is at body temperature or higher.

Document U.S. Pat. No. 3,669,880 discloses a recirculating dialysate system for use with an artificial kidney in which the total volume of dialysate solution is controlled. A pump continually recirculates the dialysis solution at 200 cc per minute. After leaving the artificial kidney, the solution passes through the dialysate reservoir where it was originally introduced and where the level of solution indicates the amount of fluid removed from the body. Downstream of the dialysate reservoir, the solution is reconstituted. The reconstituted dialysate solution then passes through heater which brings the temperature of the dialysate solution up to normal body temperature and this temperature may be measured by the gauge for purposes of control.

Document U.S. Pat. No. 4,079,007 discloses a hemodialysis system comprising a modularized dialysate flow circuit manifold assembly. The dialysate solution supply and discharge means comprise a closed loop dialysate flow circuit made up of flow line segments which join the dialyzer means with the dialysate solution supply container, for batch recirculation of the dialysate solution through the dialyzer means. The dialysate solution is advanced through the dialysate solution flow circuit at rate for example of about 500 milliliters/minute. From the supply container, the dialysate solution is withdrawn and passed to heating means wherein the dialysate solution is heated. Such heating is carried out to yield a proper dialysate solution temperature to prevent undue heating or cooling of the blood by heat exchange with the dialysate solution and to prevent hemolysis.

Document WO 2014121157 discloses a flow loop for hemodialysis, hemodiafiltration and hemofiltration for the treatment of pathological conditions provided with a heater. A temperature sensor is used for closed loop control of dialysate temperature by action of the controller and heater. The temperature of the dialysis solution is controlled to achieve the correct disinfection temperature or to determine the sodium bicarbonate concentration.

Document U.S. Pat. No. 3,809,241 discloses a kidney dialysis apparatus for the dialysis of blood comprising: dialysate supply means; artificial kidney means; a recirculation pump having dialysate solution input and output terminals, said dialysate solution input terminal coupled to said dialysate supply means; and heat reclaiming means thermally coupled to said heat source for transferring the heat dissipated by said heat source to said dialysate solution. The heat reclaiming unit provides for sufficient transfer of heat to the dialysate solution to maintain the dialysate solution at an appropriate temperature of approximately 37 DEG C.

Document U.S. Pat. No. 5,863,421 discloses a hemodialysis machine. The machine is provided with a dialyzer and with a large tank where purified water is premixed with dry chemicals to make dialysis solution, which is warmed and recirculated through the dialyzer dialysate path. Pump pumps fresh dialysate through heater where it is heated to 37 degrees ° C. and pumped through the dialysate circuit and back to the tank. Heater assembly is a temperature controlled, flow-through heater. The heater controls the dialysate temperature to the prescribed temperature. A filter creates a negative pressure which causes entrapped air to come out of the water.

The solutions proposed by the cited prior art documents are not able to provide warming performances similar to blood warmers acting directly on the blood circuit, in particular when the fluid exchange rate becomes low, sometimes with the impossibility to compensate for the heat losses to atmosphere of said blood circuit.

Furthermore, the solutions proposed by the cited prior art documents are not able to control with high accuracy the temperature of blood heated through the dialysate.

Both these defects may deteriorate the comfort of the patient under treatment.

SUMMARY OF THE INVENTION

In view of the above, it is an object of the present invention to increase the performance of the known warming systems for indirect blood warming which heat fluids and exploit the heat exchange between said fluids and blood at the treatment unit. It is a further object of the present invention to increase the warming powers delivered by said systems. In particular, it is an object of the present invention to provide better warming in case of low fluid exchange rate.

It is a further object of the present invention to improve the blood temperature control provided by said systems.

It is a further object of the present invention to improve the safety of said systems.

It is a further object of the present invention to provide a warming system which is simple, reliable and easy to design. At least one of the above objects is substantially achieved by providing a recirculation loop connected to the secondary chamber of the treatment unit together with a warming device configured to warm a portion of said recirculation loop and with a control unit configured to monitor the blood temperature and to adjust said blood temperature by controlling warming of the recirculation loop and/or the flow rate in said recirculation loop.

Aspects of the invention are disclosed in the following.

In accordance with a $1^{st}$ independent aspect, an extracorporeal blood treatment apparatus comprises:
a blood treatment device comprising a blood chamber and a fluid chamber separated from one another by a semipermeable membrane;
an extracorporeal blood circuit comprising a blood withdrawal line connected to an inlet port of the blood chamber and a blood return line connected to an outlet port of the blood chamber;
a blood pump configured to be coupled to the blood withdrawal line;
a closed fluid line connected to an inlet port of the fluid chamber and to an outlet port of the fluid chamber, wherein the closed fluid line together with the fluid chamber forms a recirculation loop;
an evacuation line departing from the closed fluid line to receive waste fluid coming from the fluid chamber;
a fluid warming device coupled or configured to be coupled to the closed fluid line;
a recirculation pump coupled or configured to be coupled to the closed fluid line;
at least one blood temperature sensor operative on the extracorporeal blood circuit and configured to sense a blood temperature;
a control unit connected to the fluid warming device, to the recirculation pump and to said at least one temperature sensor;
wherein the control unit is configured to execute the following procedure:
receiving from the blood temperature sensor at least a signal correlated to the blood temperature;
adjusting said blood temperature by controlling at least one of the fluid warming device and the recirculation pump.

In accordance with a $2^{nd}$ independent aspect, a method of controlling blood warming in an extracorporeal blood circuit of an extracorporeal blood treatment apparatus comprises:
recirculating a fluid in a recirculation loop through a recirculation pump coupled or configured to be coupled to the recirculation loop;
wherein a fluid chamber of a blood treatment device is part of said recirculation loop, wherein the blood treatment device comprises a blood chamber separated from the fluid chamber by a semipermeable membrane, wherein an extracorporeal blood circuit is connected to an inlet port of the blood chamber and to an outlet port of the blood chamber;

warming the fluid in the recirculation loop through a fluid warming device operating on said recirculation loop;

receiving from a blood temperature sensor operative on the extracorporeal blood circuit at least a signal correlated to the blood temperature;

adjusting said blood temperature by controlling at least one of the fluid warming device and the recirculation pump.

The recirculation loop on the fluid circuit allows to constantly maintain a significant fluid flow rate in the fluid chamber of the blood treatment device. Warming of said recirculation loop allows then for an efficient warming of blood. Flow in the recirculation loop as well as temperature at the warming device outlet may be modulated according to the desired blood warming level.

In a $3^{rd}$ aspect according to any of the previous two aspects, adjusting the blood temperature comprises: bringing and keeping the blood temperature to a preset blood temperature.

In a $4^{th}$ aspect according to previous aspect 3, the preset blood temperature is equal to or close to the body temperature.

In a $5^{th}$ aspect according to any the previous aspect 3 or 4, the preset blood temperature is comprised between about 36° C. and 39° C.

In a $6^{th}$ aspect according to any of the previous aspects form 1 to 5, the blood temperature sensor is placed on the blood return line.

In a $7^{th}$ aspect according to any of the previous aspects from 1 to 6, the blood temperature sensor is placed close to the outlet port of the blood chamber and it is configured to sense a blood outlet temperature.

In a $8^{th}$ aspect according to any of the previous aspects from 1 to 7, adjusting the blood temperature comprises: regulating a fluid flow rate in the recirculation loop, optionally in a recirculation pump section of the recirculation loop, by controlling the recirculation pump.

In a $9^{th}$ aspect according to any of the previous aspects from 1 to 8, the recirculation pump is a peristaltic pump and adjusting the blood temperature comprises: regulating a recirculation pump flow rate, optionally a rotational speed of the recirculation pump.

In a $10^{th}$ aspect according to the previous aspect 8 or to aspect 9 when refers to aspect 8, the fluid flow rate in the recirculation loop is greater than about 5 ml/min, optionally greater than about 50 ml/min, optionally greater than about 200 ml/min.

In a $11^{th}$ aspect according to any of the previous aspects from 1 to 10, the warming device is controlled to set a fluid temperature in the recirculation loop to a preset fluid temperature.

In a $12^{th}$ aspect according to any of the previous aspects from 1 to 11, the apparatus comprises a fluid temperature sensor connected to the control unit, wherein said fluid temperature sensor is operative on the closed fluid line and it is configured to sense a fluid temperature.

In a $13^{th}$ aspect according to the previous aspect, said fluid temperature sensor is placed at an outlet of the fluid warming device.

In a $14^{th}$ aspect according to any of the previous aspects from 1 to 13, adjusting the blood temperature comprises: regulating a fluid temperature in the recirculation loop by controlling the fluid warming device.

In a $15^{th}$ aspect according to any of the previous aspects from 1 to 14, adjusting the blood temperature comprises: regulating a fluid temperature at an outlet of the fluid warming device.

In a $16^{th}$ aspect according to any of the previous aspects from 1 to 15, adjusting the blood temperature comprises: regulating a temperature of the fluid warming device.

In a $17^{th}$ aspect according to any of the previous aspects from 1 to 16, adjusting the blood temperature comprises: regulating a power of the fluid warming device.

In a $18^{th}$ aspect according to any of the previous aspects 14 and from 15 to 17 when referring to aspect 14, the fluid temperature at an outlet of the fluid warming device is higher than a preset blood temperature.

In a $19^{th}$ aspect according to the previous aspect, the fluid temperature at an outlet of the fluid warming device is comprised between about 38° and about 42° C.

In a $20^{th}$ aspect according to any of the previous aspects form 1 to 19, the recirculation pump is controlled to set a fluid flow rate in the recirculation loop to a preset fluid flow rate.

In a $21^{st}$ aspect according to any of the previous aspects from 1 to 20, adjusting the blood temperature comprises:

setting a fluid flow rate in a recirculation pump section of the recirculation loop to zero;

regulating a fluid temperature at an outlet of the fluid warming device;

if said fluid temperature is at a maximum and a preset blood temperature is not reached, keeping the fluid temperature at the maximum and increasing the fluid flow rate in the recirculation loop till the preset blood temperature is reached.

In a $22^{nd}$ aspect according to any of the previous aspects from 1 to 21, the warming device is placed downstream of the recirculation pump on the closed fluid line.

In a $23^{rd}$ aspect according to any of the previous aspects from 1 to 22, the apparatus comprises a dialysis line connected to the closed fluid line for supplying a fresh treatment fluid to the inlet port of the fluid chamber.

In a $24^{th}$ aspect according to the previous aspect, the dialysis line is connected upstream of the warming device, optionally between the warming device and the recirculation pump.

In a $25^{th}$ aspect according to any of the previous aspects from 1 to 24, the evacuation line is connected upstream of the recirculation pump, optionally between the outlet port of the fluid chamber and said recirculation pump.

In a $26^{th}$ aspect according to the previous aspect 25 when referring to aspects 23 or 24, the dialysis line is connected between the recirculation pump and the evacuation line.

In a $27^{th}$ aspect according to the previous aspect, a fluid flow rate in the recirculation loop is equal to or greater than a dialysate flow rate in the dialysis line.

In a $28^{th}$ aspect according to aspect 23, the dialysis line is connected downstream of the warming device.

In a $29^{th}$ aspect according to the previous aspects, an air trap is operative on the closed fluid line. The air trap allows to manage air generated by degassing due to fluid warming. Furthermore the recirculation loop and associated control system may be designed as to allow for periodical removal of air bubbles generated or trapped inside the membrane 5.

In a $30^{th}$ aspect according to the previous aspect, the control unit is configured to execute a degassing procedure of the membrane of the blood treatment device.

In a $31^{st}$ aspect according to the previous aspects 29 or 30, the air trap is located downstream of the fluid warming device, optionally between the fluid warming device and the inlet port of the fluid chamber.

In a $32^{nd}$ aspect according to the previous aspect when refers to aspect 30, the degassing procedure comprises:

controlling the recirculation pump to reverse the fluid flow in the recirculation loop, optionally to pump fluid at a maximum fluid flow rate.

In a 33$^{rd}$ aspect according to the previous aspects 29 or 30, the air trap is located upstream of the recirculation pump, optionally between the recirculation pump and the outlet port of the fluid chamber.

In a 34$^{th}$ aspect according to the previous aspect, the evacuation line departs from said air trap.

In a 35$^{th}$ aspect according to aspects 33 or 34 when aspect 33 refers to aspect 30, the degassing procedure comprises: controlling the recirculation pump to pump fluid at a maximum fluid flow rate.

In a 36$^{th}$ aspect according to aspects 32 or 35, the maximum fluid flow rate is comprised between about 200 ml/min and about 300 ml/min.

In a 37$^{th}$ aspect according to aspects 32 or 35, the degassing procedure is performed for a degassing time period, optionally of about 1 min.

In a 38$^{th}$ aspect according to the previous aspects from 29 to 37, the air trap comprises a service line and air accumulated in the air trap is removed through said service line. Optionally, if the evacuation line departs from said air trap as recited in aspect 34, said evacuation line may be used as to remove air bubbles simultaneously to the 'waste' fluid.

In a 39$^{th}$ aspect according to the previous aspects from 29 to 37, the air trap comprises a hydrophobic membrane and said air trap is vented passively.

In a 40$^{th}$ aspect according to the previous aspects, the apparatus comprises at least one post-infusion line connected to the blood return line.

In a 41$^{st}$ aspect according to the previous aspect, the post-infusion line is connected between the outlet port of the blood chamber and the blood temperature sensor. The blood return temperature is measured downstream of the post-infusion line.

In a 42$^{nd}$ aspect according to the previous aspects, the apparatus comprises one pre-infusion line connected to the blood withdrawal line, optionally between the blood pump and the inlet of the blood chamber.

In a 43$^{rd}$ aspect according to the previous aspect, the pre-infusion line is connected downstream of an auxiliary blood temperature sensor.

In a 44$^{th}$ aspect according to the previous aspects, the apparatus comprises one pre-pump infusion line connected to the blood withdrawal line upstream of the blood pump.

Warming of the recirculation loop allows for an efficient warming of blood even in the case where the fluid infusions are stopped, by simply continuing running the recirculation pump and the fluid warming device.

In a 45$^{th}$ aspect according to the previous aspects from 40 to 44, at least one among the post-infusion line, the pre-infusion line and the pre-pump infusion line passes through the fluid warming device to heat the infusion fluid before reaching the blood circuit.

In a 46$^{th}$ aspect according to the previous aspect, the fluid warming device comprises a first portion operative on the closed fluid line and a second portion operative on said at least one among the post-infusion line, the pre-infusion line and the pre-pump infusion line.

In a 47$^{th}$ aspect according to the previous aspects from 40 to 46, the apparatus comprises an heat exchanger placed on the closed fluid line, wherein at least one among the post-infusion line, the pre-infusion line and the pre-pump infusion line passes through said heat exchanger to exchange heat with the fluid in the closed fluid line before reaching the blood circuit.

In a 48$^{th}$ aspect according to the previous aspect, the heat exchanger is placed downstream of the fluid warming device. In the case of high infusion flow rate to blood flow rate ratio, the infusion cooling effects are balanced by heating the infusion fluid/s exploiting the same warming device on the closed fluid line.

In a 49$^{th}$ aspect according to anyone of the previous aspects, the control unit is further configured to ultrafilter blood by removing plasma water from blood in the extracorporeal blood circuit and discharge excess fluid through the evacuation line.

In a 50$^{th}$ aspect according to anyone of the previous aspects, the control unit is further configured to ultrafilter blood by removing plasma water from blood in the extracorporeal blood circuit through the blood treatment device and the evacuation line.

In a 51$^{st}$ aspect according to anyone of the previous aspects, the control unit (25) is further configured to ultrafilter blood by removing plasma water from blood in the extracorporeal blood circuit and contemporaneously to re-circulate fluid in the recirculation loop.

In a 52$^{nd}$ aspect according to anyone of the previous aspects, the closed fluid line (10) and the evacuation line (15) are arranged to allow recirculation of fluid in the recirculation loop and selective fluid removal from the closed fluid line (10) via the evacuation line (15) while fluid is recirculating in the recirculation loop.

In a 53$^{rd}$ aspect according to anyone of the previous aspects, the control unit is configured to allow recirculation of fluid in the recirculation loop and selective fluid removal from the closed fluid line (10) via the evacuation line (15) during fluid recirculation in the recirculation loop.

DESCRIPTION OF THE DRAWINGS

The following drawings relating to aspects of the invention are provided by way of non-limiting example:

FIG. 5 shows a flow chart of a procedure for blood warming control;

DETAILED DESCRIPTION

Figure 1:
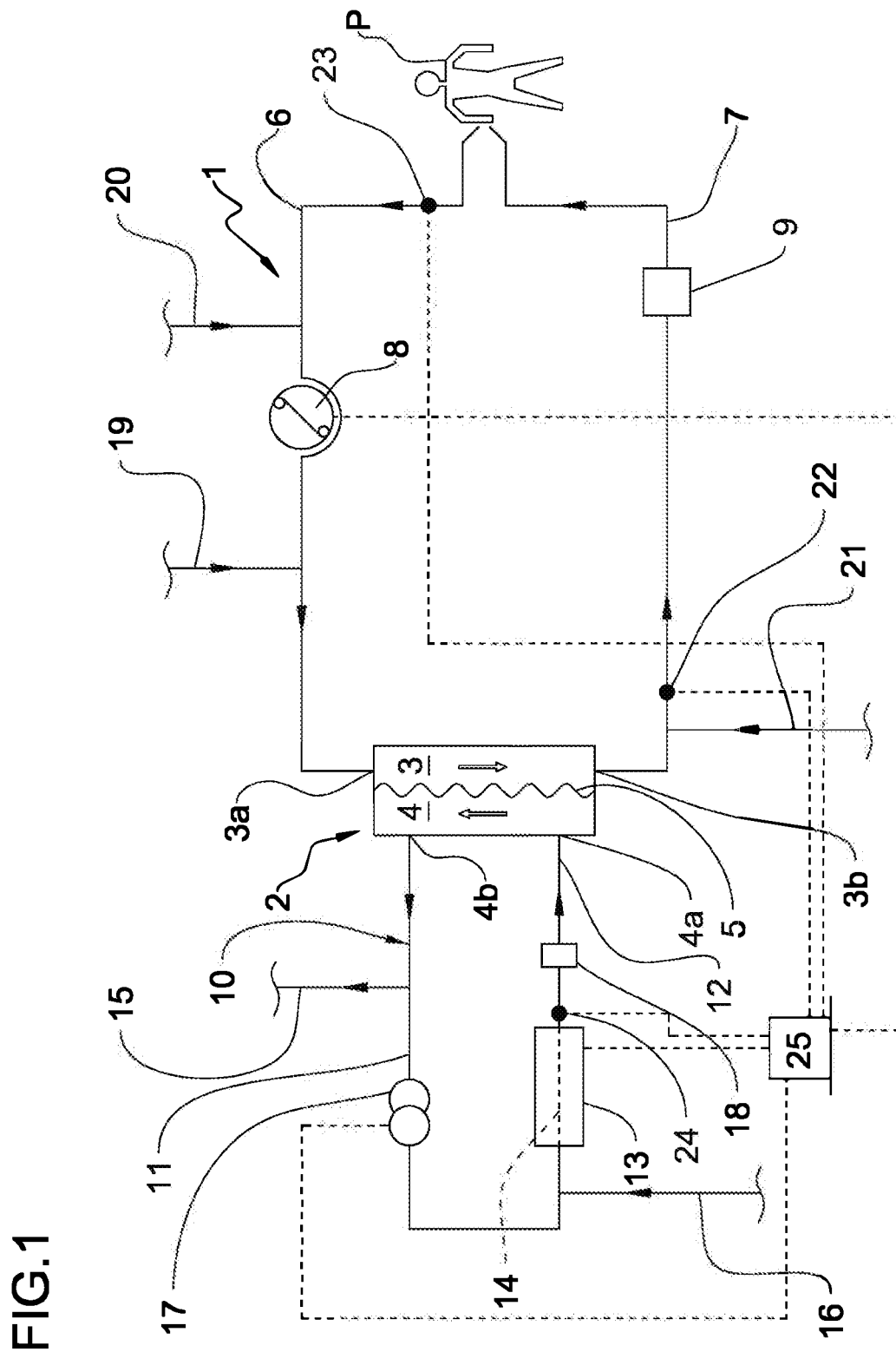
FIG. 1 shows a schematic representation of an extracorporeal blood treatment apparatus provided with a recirculation loop according to the invention.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6. When rotated, e.g., clockwise, the blood pump 8 causes a flow of blood along the blood withdrawal line 6 towards the blood chamber 3 (see the arrows in FIG. 1 indicative of the blood flow along the blood withdrawal line 6).

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device 9 operating on the blood return line 7 (the air trapping device 9 is a venous deaeration chamber). The air trapping device 9 is placed online in the blood return line 7.

A first section of the blood return line 7 puts in fluid communication the outlet port 3b of the blood chamber 3 with the air trapping device 9 and a second section of the blood return line 7 puts in fluid communication the air trapping device 9 with the patient P. The blood coming from the blood chamber 3 of the treatment device 2 enters and exits the air trapping device 9 before reaching the patient P.

The apparatus 1 further comprises a closed fluid line 10 connected to an inlet port 4a of the fluid chamber 4 and to an outlet port 4b of said fluid chamber 4. In other words, the closed fluid line 10 comprises a first section 11 connected to the outlet port 4b and departing from the fluid chamber 4 and a second section 12 connected to the inlet port 4a and joined to said fluid chamber 4. The second section 11 develops uninterrupted from the first section 11 and, in the attached non limiting figures, the closed fluid line 10 is "U" shaped. The closed fluid line 10 together with the fluid chamber 4 forms a recirculation loop for at least part of the fluid flowing through the fluid chamber 4.

A fluid warming device 13 is coupled to the closed fluid line 10. The fluid warming device 13 is schematically represented in the annexed figures. The fluid warming device 13 is associated with the apparatus 1 to form an assembly which is structured to treat fluid and keep fluid within predetermined desired temperature boundaries. The fluid warming device 13 may comprise a warmer provided with a heating unit which cooperates with a heated section 14 of the closed fluid line 10. This heated section 14 may be a tube or a bag or a cassette part of the closed fluid line 10 or part of the warmer itself. The fluid warming device 13 may be an independent device (e.g. a stand alone unit physically separated from the apparatus 1) cooperating with the apparatus 1 and—in particular—warming the heated section 14 of the closed fluid line 10. Alternatively, the fluid warming device 13 may be a component of the apparatus 1. In this case the fluid warming device 13 is not an independent stand alone unit, but rather part of the apparatus 1. In practice the heating unit has heating elements (e.g. electric impedances, infrared emitters or other types of heating elements) configured to heat the corresponding heated section 14 of the closed fluid line 10.

The apparatus 1 of FIG. 1 further comprises one fluid evacuation line 15 connected with an outlet port 4b of the fluid chamber 4 through the first section 11 of the closed fluid line 10 such as to receive at least part of a filtered waste fluid through the semipermeable membrane 5. The fluid evacuation line 15 receives such filtered waste fluid coming from the fluid chamber 4 of the treatment device 2, for example, comprising used dialysis liquid and/or liquid ultrafiltered through the membrane 5. The fluid evacuation line 15 leads to a receiving element, not shown, for example having a collection bag or a drainage pipe for the waste fluid. One or more dialysate pumps, not shown, may operate on the evacuation line 15.

In the example of FIG. 1, a dialysis line 16 is also present, for supplying a fresh treatment fluid into the closed fluid line 10 and then into the inlet port 4a of the fluid chamber 4. The presence of this dialysis line 16 is not strictly necessary since, in the absence of the dialysis line 16, the apparatus 1 is still able to perform treatments such as ultrafiltration, hemofiltration or plasma-filtration. In case the dialysis line 16 is present, a fluid flow intercept device may be used, not shown, to selectively allow or inhibit fluid passage through the dialysis line 16, depending on whether or not a purification by diffusive effect is to be performed inside the treatment device 2.

The dialysis line 16, if present, is typically equipped with a dialysis pump, not shown, and is able to receive a fresh fluid from a module, for example a bag or on-line preparation section of dialysis fluid, and to send such a fluid to the inlet port 4a of the fluid chamber 4. The fluid evacuation line 10, the dialysis line 16, the closed fluid line 10 and the fluid chamber 4 are part of a treatment fluid circuit.

A recirculation pump 17 is coupled to the closed fluid line 10 and operates to cause movement of the fluid in said closed fluid line 10 from the outlet port 4b of the fluid chamber 4 through the first section 11 and through the second section 12 of the closed fluid line 10 to the inlet port 4a of the fluid chamber 4 and, inside said fluid chamber 4, from the inlet port 4a towards the outlet port 4b. The recirculation pump 17 is, for example, a peristaltic pump which acts on a respective pump section of the closed fluid line 10. When rotated, e.g., clockwise, the recirculation pump 17 causes a flow of fluid counterclockwise in recirculation loop (see arrows in FIG. 1). The recirculation loop on the fluid circuit allows to constantly maintain a significant fluid flow rate in the fluid chamber 4 of the blood treatment device 2.

The fluid evacuation line 15 is connected to the closed fluid line 10 between the outlet port 4b and said recirculation pump 17. The fluid warming device 13 is placed between the recirculation pump 17 and the inlet port 4a. The dialysis line 16 is connected to the closed fluid line 10 between the fluid warming device 13 and the recirculation pump 17.

Downstream of the fluid warming device 13 (with respect to the counterclockwise flow of fluid in the recirculation loop), between the warming device 13 and the inlet port 4a, an air trap 18 is placed on the closed fluid line 10 to manage air generated by degassing due to fluid warming.

The apparatus 1 as shown comprises an infusion circuit comprising one or more infusion lines of a replacement fluid. According to the embodiment of FIG. 1, a pre-infusion line 19 is connected to the blood withdrawal line 6 between the blood pump 8 and the inlet port 3a of the blood chamber 3. A pre-pump infusion line 20 is connected to the blood withdrawal line 6 upstream of the blood pump 8, between said blood pump 8 and the vascular access device inserted in the fistula on the patient P. A post-infusion line 21 is connected to the blood return line 7 upstream of the air trapping device 9. Infusion pump or pumps, not shown, equips the infusion circuit. Each of the pre- and/or post-infusion lines 19, 20, 21 may be provided with a respective pump. The pre- and/or post-infusion lines 19, 20, 21 may be supplied by fluid coming from bags or directly by infusion fluid prepared on-line.

The apparatus 1 comprises a blood temperature sensor 22 operative on the extracorporeal blood circuit and configured to sense a blood temperature. The blood temperature sensor 22 is placed on the blood return line 7. The blood temperature sensor 22 is placed so close to the outlet port 3b of the blood chamber 3 to sense the temperature of the blood coming out of the blood chamber 3. The blood temperature sensor 22 is placed downstream of the post-infusion line 21, between said post-infusion line 21 and the air trapping device 9. The post-infusion line 21 is connected between the outlet port 3b of the blood chamber 3 and the blood temperature sensor 22.

The apparatus 1 comprises an auxiliary blood temperature sensor 23 operative on the withdrawal line 6 close to the patient P to sense the temperature of the blood withdrawn from the patient P. The pre-infusion line 19 is connected downstream of the auxiliary blood temperature sensor 23.

The apparatus 1 comprises a fluid temperature sensor 24 operative on the closed fluid line 10 and configured to sense a fluid temperature in the closed fluid line 10. The fluid temperature sensor 24 of FIG. 1 is placed so close to an outlet of the fluid warming device 13 to sense the temperature of the fluid coming out of said fluid warming device 13. According to an embodiment not shown, said fluid temperature sensor 24 may also be part of the fluid warming device 13, embedded in a frame or casing of the fluid warming device 13. The apparatus 1 comprises a control unit 25 which may comprise a digital processor (CPU) and memory (or memories), an analog circuit, or a combination thereof. The control unit 25 is connected to the blood pump 8 and may be configured to control the blood pump 8 based, by way of example, on a set blood flow rate. The control unit 25 of the apparatus 1 may also be configured to control the flow rate of dialysis fluid through the dialysis line 16, of evacuation fluid through the evacuation line 15, of infusion fluid/s through pre-infusion line 19, the pre-pump infusion line 20 and post-infusion line 21.

The control unit 25 is also connected to the recirculation pump 17 and to the fluid warming device 13 and it is configured to control said recirculation pump 17 and said fluid warming device 13 in order to adjust the temperature of blood in the blood circuit.

To this aim, the control unit 25 is also connected to the blood temperature sensor 22, to the auxiliary blood temperature sensor 23 and to the fluid temperature sensor 24. In use and according to the procedure and method of the invention, warming of blood is performed through warming of fluid in the recirculation loop.

A preset/target blood temperature Tbp at the outlet 3a of the blood chamber 3 is entered into the control unit 25 or previously saved in the memory of the control unit 25. Said preset blood temperature Tbp may be the body temperature or close to the body temperature. Said preset blood temperature Tbp may of about 37° C. In order to take into account the heat losses downstream of the blood temperature sensor 22, said preset blood temperature Tbp may be higher than the body temperature, for example of about 38° C.

Fluid flow rate Qr in the recirculation loop as well as fluid temperature Tf at the outlet of the warming device are modulated to reach and keep the preset/target blood temperature Tbp at the outlet 3a of the blood chamber 3. During treatment, the control unit 25 continuously receives from the blood temperature sensor 22 a signal correlated to the blood temperature Tb at the outlet 3b of the blood chamber 3. The control unit 25 controls at least one of the fluid warming device 13 and the recirculation pump 17 to bring and keep the measured blood temperature Tb equal to or close to the preset blood temperature Tbp.

Example 1

According to one example of the procedure performed by the apparatus of FIG. 1, the fluid flow rate Qr in the recirculation loop 10 is fixed to a preset fluid flow rate Qrp, by maintaining a fixed rotational speed of the recirculation pump 17, and the fluid temperature Tf at the outlet of the warming device 13 is regulated in order to bring and keep the measured blood temperature Tb at the outlet 3a of the blood chamber 3 equal to or at least close to the preset blood temperature Tbp (flow chart of FIG. 5). The control unit 25 may regulate a power of the fluid warming device 13 to bring and keep the measured blood temperature Tb equal to or at least close to the preset blood temperature Tbp.

The control unit 25 receives from the fluid temperature sensor 24 a signal correlated to the fluid temperature Tf at the outlet of the warming device 13.

A maximum fluid temperature Tfmax at the outlet of the warming device 13 is set (by way of example to 42° C.) The control unit 25 controls the power of the fluid warming device 13 so that the fluid temperature Tf does not exceed said maximum fluid temperature Tfmax.

The following table 1 shows the outcome in the case of the recirculation loop of FIG. 1 is operated at a fixed fluid flow rate Qr and the fluid temperature Tf at the outlet of the warming device 13 is adjusted as to deliver the desired/preset outlet blood temperature Tbp. The 66 ml/min fixed fluid flow rate Qr is chosen as the minimum flow allowing to deliver the preset 38° C. outlet blood temperature Tbp in the worst case of the selected conditions (Qb=200 ml/min, Qd=0). Qb (ml/min) is the blood flow rate in the blood circuit. Qd (ml/min) is the flow rate of dialysate in the dialysis line 16.

For the sake of simplicity, the following additional assumptions are used:
  temperature of the blood flowing into the blood chamber (Tbi) is taken as 36° C., blood treatment device (Hemodialyzer) surface area (S) is taken as 1.5 m², preset blood temperature (Tbp) is taken as 38° C., as to anticipate cooling effects present in the return line 7, maximum fluid temperature (Tfmax) is set to 42° C., in accordance with IEC 60601-2-16 standard default recommendations.

TABLE 1

| | Qr = 66 ml/min | | | | | | | |
|---|---|---|---|---|---|---|---|---|
| | Qb (ml/min) | | | | | | | |
| | 100 | | | | 200 | | | |
| Qd (ml/min) | 0 | 25 | 50 | 75 | 0 | 25 | 50 | 75 |
| Tf ° C. | 39.0 | 39.5 | 38.2 | 38.1 | 42.0 | 40.4 | 39.5 | 39.0 |
| Tb ° C. | 38.0 | 38.0 | 38.0 | 38.0 | 38.0 | 38.0 | 38.0 | 38.0 |

Example 2

According to another example of the procedure performed by the apparatus of FIG. 1, a fluid temperature Tf at the outlet of the warming device 13 is fixed to a preset fluid temperature Tfp, which may be the maximum fluid temperature Tfmax, by controlling the power of the warming device 13.

Figure 6:
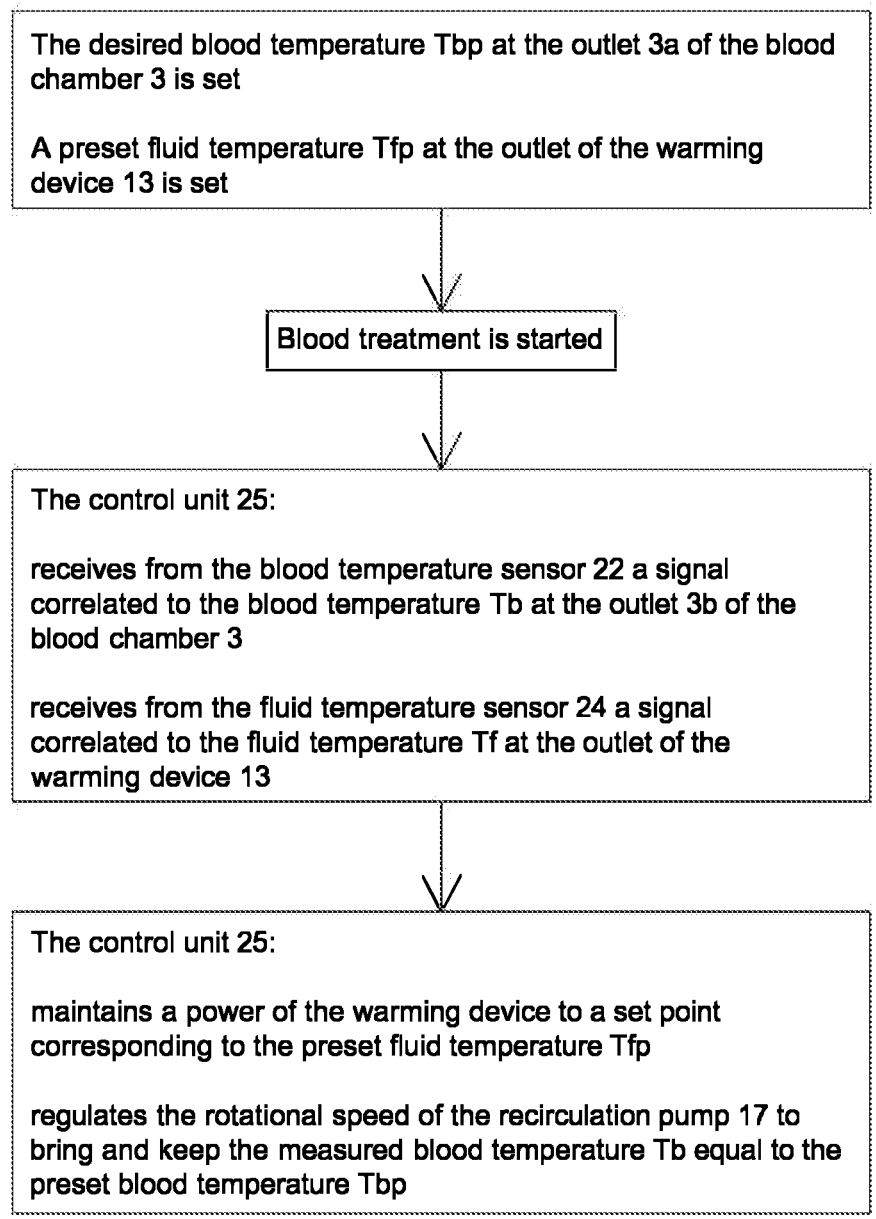
FIG. 6 shows a flow chart of another procedure for blood warming control.

The fluid flow rate Qr in the recirculation loop is regulated in order to bring and keep the measured blood temperature Tb at the outlet 3b of the blood chamber 3 equal to or at least close to the preset blood temperature Tbp (flow chart of FIG. 6). The control unit 25 may regulate the rotational speed of the recirculation pump 17 to bring and keep the measured blood temperature Tb equal to or at least close to the preset blood temperature Tbp.

Table 2 shows that the fluid flow rate Qr is minimized by having the warming device 13 operating at its maximum set point when non-zero fluid flow rate Qr is used to get the desired preset blood temperature Tbp. In these conditions, much lower fluid flow rates Qr than the 66 ml/min of table 1 may be used as soon as dialysate flow is not zero.

TABLE 2

| | Qb (ml/min) | | | | | | | |
|---|---|---|---|---|---|---|---|---|
| | 100 | | | | 200 | | | |
| Qd (ml/min) | 0 | 25 | 50 | 75 | 0 | 25 | 50 | 75 |
| Qr (ml/min) | 33 | 8.5 | 0 | 0 | 66 | 42 | 17 | 0 |
| Tfmax ° C. | 42.0 | 42.0 | 40.0 | 38.7 | 42.0 | 42.0 | 42.0 | 41.3 |
| Tb ° C. | 38.0 | 38.0 | 38.0 | 38.0 | 38.0 | 38.0 | 38.0 | 38.0 |

Example 3

Figure 7:
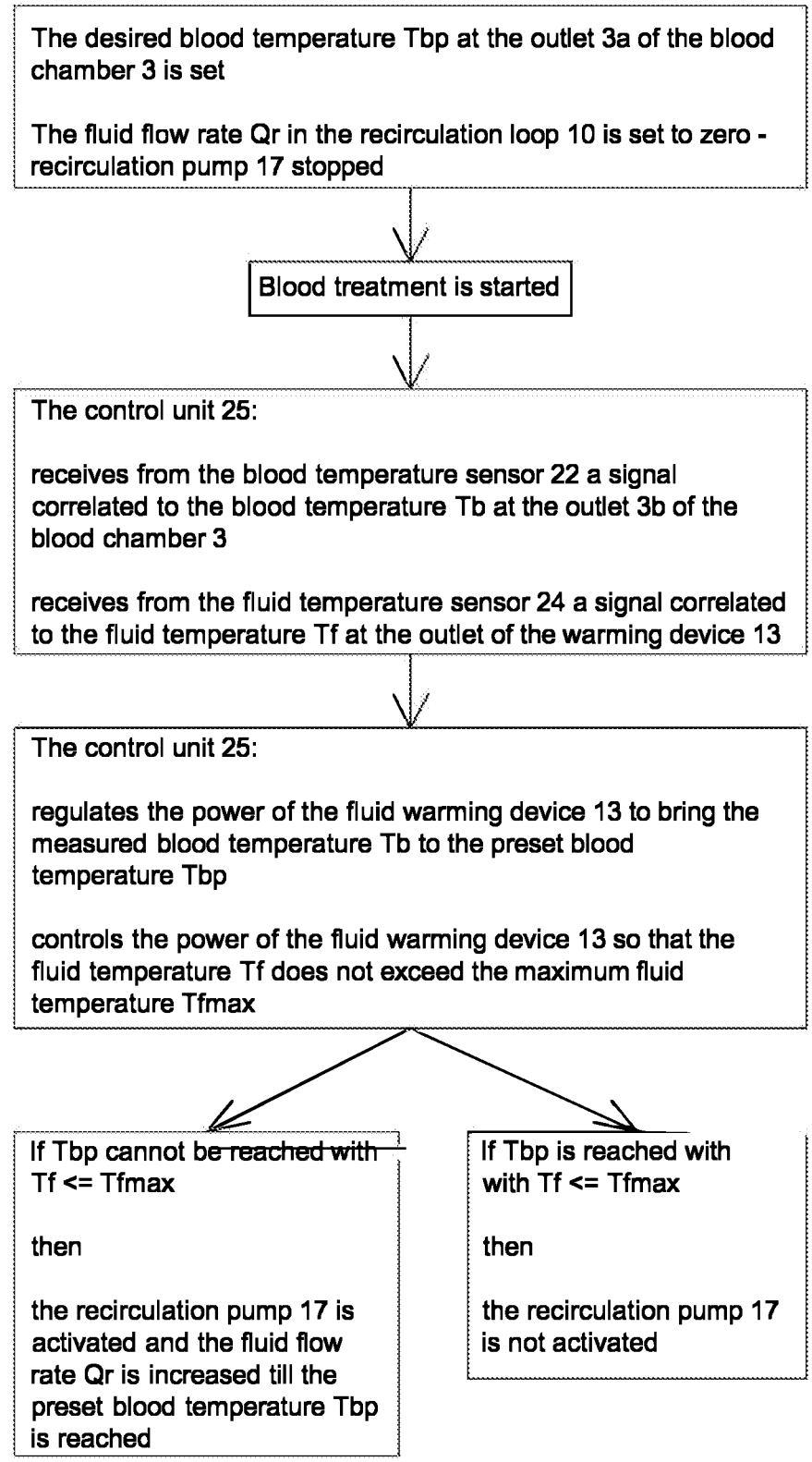
FIG. 7 shows a flow chart of another procedure for blood warming control.

According to another example of the procedure performed by the apparatus of FIG. 1, the control unit 25 may operate as follows (flow chart of FIG. 7):
 starting patient blood treatment with no recirculation (setting the fluid flow rate Qr in the recirculation loop 10 to zero, recirculation pump 17 stopped) and adjusting the fluid temperature Tf at the outlet of the warming device 13 according to the desired/preset blood temperature Tbp;
 if the preset blood temperature Tbp is reached with the fluid temperature Tf lower than or equal to the maximum Tfmax, the recirculation pump 17 is not activated;
 if the preset blood temperature Tbp cannot be reached with the fluid temperature Tf at the maximum Tfmax and with no recirculation, keeping the fluid temperature Tf at the maximum Tfmax and increasing step by step the fluid flow rate Qr in the recirculation loop 10 (the recirculation pump 17 is activated) till the preset blood temperature Tbp is reached.

This procedure allows to minimize performance loss in term of dialyzer clearance (with no measurable performance loss for small solutes like urea and about 10% losses for large solutes like inulin) with respect to a conventional apparatus with no recirculation loop. For sake of clarity, the system dialyzer clearance is defined as the volume of plasma or blood from which a given substance has been removed completely in a given time period. The dialyzer clearance of a substance depends on four factors: 1. Surface area of the dialyzer. 2. Blood flow rate. 3. Dialysate flow rate. 4. Permeability of that substance with respect to the dialyzer membrane.

The extracorporeal blood treatment apparatus of FIG. 1 may also be configured to perform a degassing procedure of the membrane 5 (filter) of the blood treatment device 2 to allow for periodical removal of air bubbles generated or trapped inside said membrane 5.

During the degassing procedure, the control unit 25 controls the recirculation pump 17 to reverse the fluid flow in the recirculation loop. Instead of being moved, in the closed fluid line 10, from the outlet port 4b to the inlet port 4a of the fluid chamber 4, the fluid is moved from the inlet port 4a towards the outlet port 4b with a maximum fluid flow rate of about 300 ml/min and for a time period of about 1 min. In this way, air bubbles from the membrane 5 are moved into the air trap 18 and then air accumulated in the air trap 18 may be removed through a service line, not shown. The removal through the service line may be fully automatic, if the air trap 18 is equipped with a level sensor and the service line is connected to a pump, or manually under the supervision of the operator. Alternatively, air trapped in the air trap 18 may be vented 'passively' through a hydrophobic membrane, provided that the absolute pressure is kept positive in the recirculation loop. This may require the addition of a pressure drop in the recirculation loop.

Figure 2:
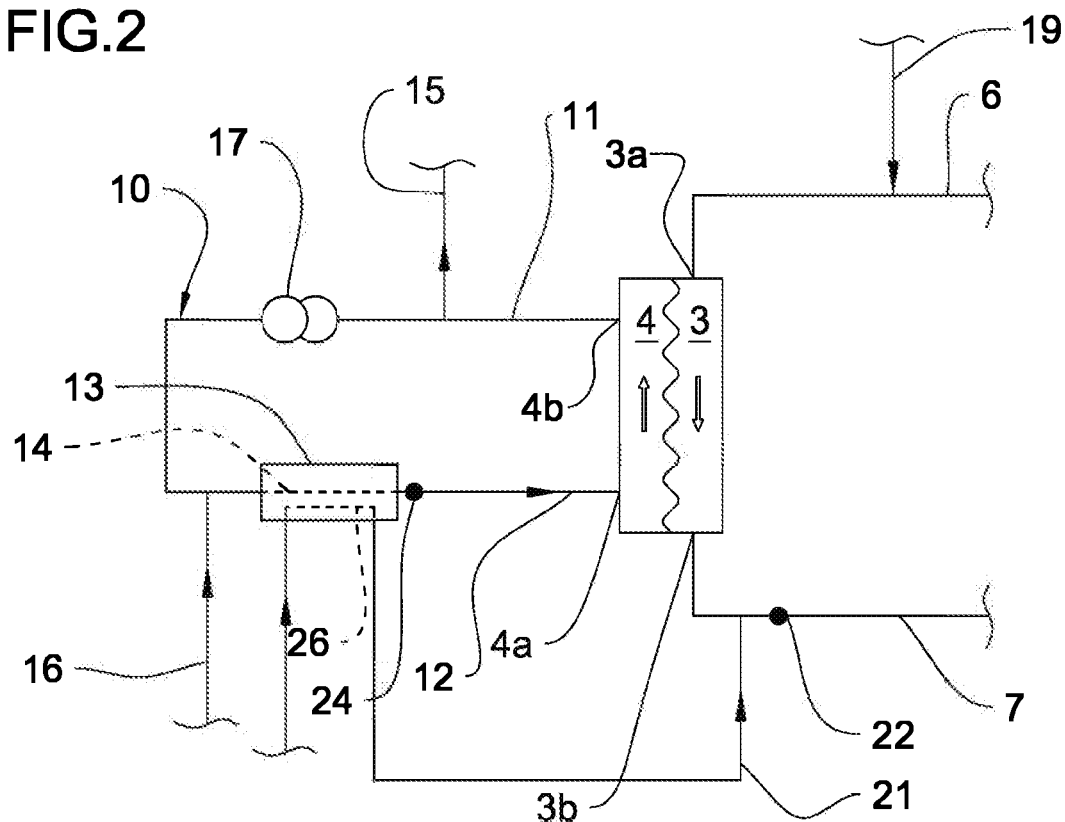
FIG. 2 shows a portion of a variant of the extracorporeal blood treatment apparatus of FIG. 1.

The extracorporeal blood treatment apparatus of FIG. 2 differs from the apparatus of FIG. 1 in that the post-infusion line 21 is operatively coupled to the warming device 13, so that said infusion fluid is heated before reaching the return line 7 of the blood circuit. FIG. 2 shows that the post-infusion line 21 passes through the fluid warming device 13 and then is connected to the blood circuit. Please note that in other not shown embodiments also the pre-infusion line 19 and the pre-pump infusion line 20 may be heated by the fluid warming device 13. The fluid warming device 13 comprises a first portion operative on the closed fluid line 10 and at least a second portion operative on said at least one among the post-infusion line 21, the pre-infusion line 19 and the pre-pump infusion line 20. Each portion of the warming device 13 may comprise a respective heating unit which cooperates with a heated section 26 of the respective infusion line 19, 20, 21. Each heating unit may be controlled separately by the control unit 25 in order to heat in different manner the closed fluid line 10 and each of the infusion line 19, 20, 21. This configuration allows for both cheaper and easier operation of the system. The combined warming device 13 may combine both hardware components (display, user interface commands, power supply, etc.) in one single device, as well as the disposable circuit components in one single article.

Figure 3:
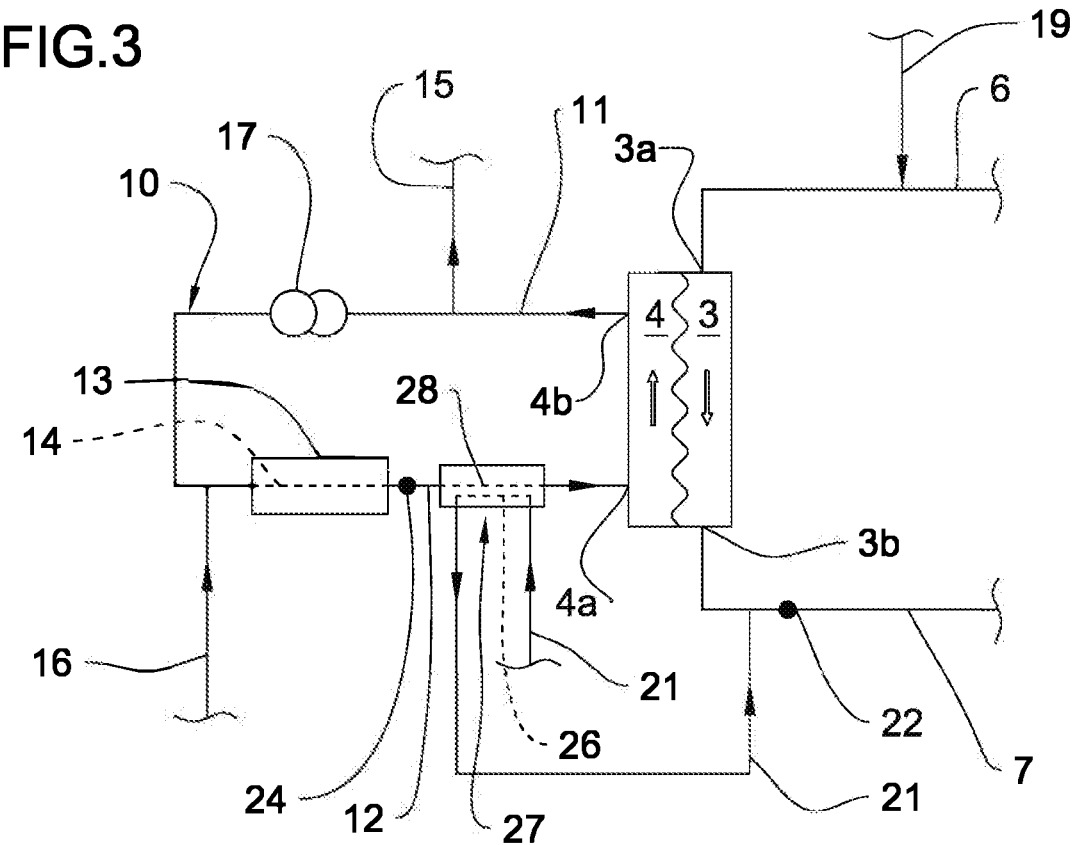
FIG. 3 shows the portion of FIG. 2 according to another variant.

The extracorporeal blood treatment apparatus of FIG. 3 differs from the apparatus of FIG. 1 in that a heat exchanger 27 is placed on the closed fluid line 10 between the fluid warming device 13 and the inlet port 4b of the fluid chamber 4. A heating section 28 of the closed fluid line 10 passes through the heat exchanger 27. A heated section 26 of the post-infusion line 21 passes through the heat exchanger 27 and then it is connected to the blood circuit. In said heat exchanger 27 the flow of fluid in the heating section 28 of the closed fluid line 10 and the flow of infusion fluid in the heated section 26 of the post-infusion line 21 flows in opposite directions (the heat exchanger is of counter-current type). The fluid in the heating section 28 of the closed fluid line 10 has just been heated in the warming device 13 and supplies heat to the infusion fluid in the heated section 26. Please note that in other not shown embodiments also the pre-infusion line 19 and the pre-pump infusion line 20 may be heated in the heat exchanger 27.

In both the embodiments of FIG. 1 and FIG. 2, the infusion fluid/s are heated exploiting the same warming device 13 which heats the recirculation loop.

Figure 4:
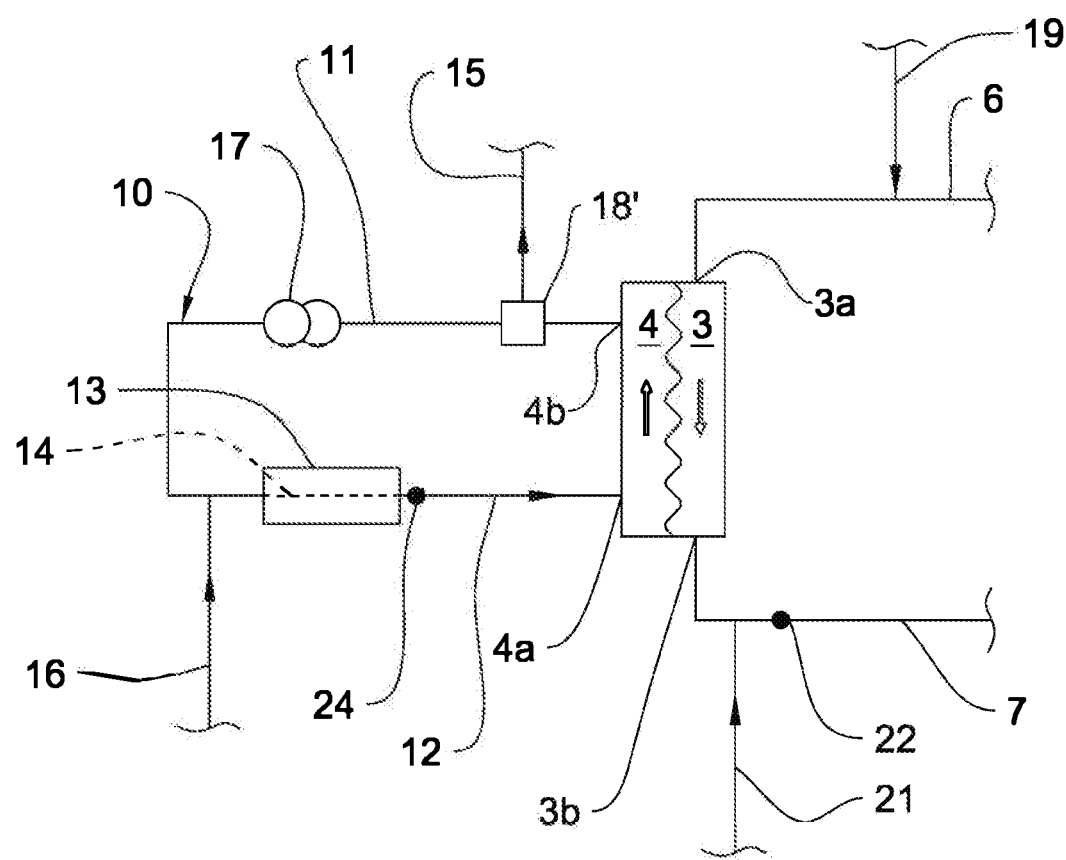
FIG. 4 shows the portion of FIG. 2 according to another variant.

The extracorporeal blood treatment apparatus of FIG. 4 differs from the apparatus of FIG. 1 in that the air trap 18' is placed between the recirculation pump 17 and the outlet 4b of the fluid chamber 4 instead of between the warming device 13 and the inlet 4a of the fluid chamber 4. Furthermore, the evacuation line 15 departs from said air trap 18'. The air trap 18' is located at the outlet port 4b of the fluid chamber 4 and the evacuation line 15 is used as to remove air bubbles simultaneously to the 'waste' fluid. In this configuration, the degassing procedure simply consists in running maximum recirculation flow rate (300 ml/min) for a short time period (typically less than 1 min).

In other not shown embodiments, dialysis line 16 may be connected to the recirculation loop between the evacuation line 15 and the recirculation pump 17. In this case, a fluid flow rate in the recirculation loop is equal to or greater than a dialysate flow rate in the dialysis line 16.

In other not shown embodiments, the dialysis line 16 is connected downstream of the warming device 13.

In other not shown embodiments, the dialysis line 16 is not present. With respect to FIG. 1 the dialysis line 16 simply disappears.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An extracorporeal blood treatment apparatus, comprising:
    A blood treatment device comprising a blood chamber and a fluid chamber separated by a semipermeable membrane;
    An extracorporeal blood circuit comprising a blood withdrawal line connected to an inlet port of the blood chamber and a blood return line connected to an outlet port of the blood chamber;
    A blood pump operable with the blood withdrawal line;
    A closed fluid line connected to an inlet port of the fluid chamber and to an outlet port of the fluid chamber, wherein the closed fluid line together with the fluid chamber form a recirculation loop;
    An evacuation line departing from the closed fluid line;
    A warming device coupled to the closed fluid line;
    A recirculation pump operable with the closed fluid line;
    At least one temperature sensor operable with the extracorporeal blood circuit to sense a blood temperature and placed adjacent to the outlet port of the blood chamber to sense a filter outlet blood temperature; and
    A control unit operably connected to the warming device, the recirculation pump, and the at least one temperature sensor, the control unit configured to:
        (i) receive, from the temperature sensor, a signal correlated to the filter outlet blood temperature measured at the outlet port of the blood chamber defining a measured filter outlet blood temperature, and
        (ii) adjust said filter outlet blood temperature measured at the outlet port of the blood chamber by controlling the warming device to regulate a fluid temperature in the recirculation loop and controlling the recirculation pump to regulate a flow rate of the recirculation pump to bring the measured filter outlet blood temperature to a preset blood temperature and maintain the measured filter outlet blood temperature at the preset blood temperature.

2. The apparatus of claim 1, wherein adjusting the filter outlet blood temperature comprises further controlling the recirculation pump and regulating a fluid flow rate in the recirculation loop by controlling the recirculation pump.

3. The apparatus of claim 1, wherein adjusting the filter outlet blood temperature includes regulating a power of the warming device.

4. The apparatus of claim 2, wherein the recirculation pump is controlled to set the fluid flow rate in the recirculation loop to a preset fluid flow rate.

5. The apparatus of claim 1, wherein adjusting the filter outlet blood temperature comprises:
    setting a fluid flow rate in a recirculation pump section of the recirculation loop to zero; and
    regulating the fluid temperature,
    wherein when said fluid temperature in the recirculation loop is at a maximum and the preset blood temperature is not reached, the control unit is configured to maintain the fluid temperature at the maximum and cause the fluid flow rate in the recirculation pump section of the recirculation loop to be increased until the preset blood temperature is reached.

6. The apparatus of claim 1, wherein the warming device is located downstream from the recirculation pump along the closed fluid line.

7. The apparatus of claim 1, further comprising a dialysis line connected to the closed fluid line for supplying a fresh treatment fluid to the inlet port of the fluid chamber, wherein the dialysis line is connected between the recirculation pump and the warming device.

8. The apparatus of claim 1, further comprising at least one of: (i) a pre-infusion line connected to the blood withdrawal line, (ii) a post-infusion line connected to the blood return line, and (iii) a pre-pump infusion line connected to the blood withdrawal line upstream of the blood pump, wherein the post-infusion line is connected between the outlet port of the blood chamber and the at least one temperature sensor.

9. The apparatus of claim 8, wherein the at least one of the post-infusion line, the pre-infusion line, and the pre-pump infusion line passes through the warming device to heat an infusion fluid before reaching the extracorporeal blood circuit.

10. The apparatus of claim 8, further comprising a heat exchanger located along the closed fluid line, wherein the at least one of the post-infusion line, the pre-infusion line, and the pre-pump infusion line passes through said heat exchanger to exchange heat with a fluid in the closed fluid line before reaching the extracorporeal blood circuit.

11. The apparatus of claim 10, wherein the heat exchanger is located downstream from the warming device.

12. The apparatus of claim 1, further comprising an air trap operable with the closed fluid line and located between the warming device and the inlet port of the fluid chamber.

13. The apparatus of claim 1, further comprising an air trap operable with the closed fluid line and located between the recirculation pump and the outlet port of the fluid chamber, wherein the evacuation line departs from said air trap.

14. The apparatus of claim 1, wherein the control unit is further configured to ultrafilter blood by causing (i) plasma water to be removed from blood in the extracorporeal blood circuit through the blood treatment device and (ii) excess fluid to be discharged through the evacuation line.

15. The apparatus of claim 1, wherein the control unit is further configured to ultrafilter blood by causing (i) plasma water to be removed from blood in the extracorporeal blood circuit through the blood treatment device, (ii) excess fluid to be discharged through the evacuation line, and (iii) fluid to be re-circulated contemporaneously in the recirculation loop.

16. An extracorporeal blood treatment apparatus comprising:
- A blood treatment device comprising a blood chamber and a fluid chamber separated by a semipermeable membrane;
- An extracorporeal blood circuit comprising a blood withdrawal line connected to an inlet port of the blood chamber and a blood return line connected to an outlet port of the blood chamber;
- A blood pump operable with the blood withdrawal line;
- A closed fluid line connected to an inlet port of the fluid chamber and to an outlet port of the fluid chamber, wherein the closed fluid line together with the fluid chamber form a recirculation loop;
- An evacuation line departing from the closed fluid line;
- A warming device coupled to the closed fluid line;
- A recirculation pump operable with the closed fluid line;
- At least one temperature sensor operable with the extracorporeal blood circuit to sense a blood temperature and placed adjacent to the outlet port of the blood chamber to sense a filter outlet blood temperature; and
- A control unit operably connected to the warming device, the recirculation pump, and the at least one temperature sensor, the control unit configured to:
  (i) Receive, from the at least one temperature sensor, a signal correlated to the filter outlet blood temperature measured at the outlet port of the blood chamber defining a measured filter outlet blood temperature,
  (ii) Adjust said filter outlet blood temperature measured at the outlet port of the blood chamber by controlling the warming device to regulate a fluid temperature in the recirculation loop and controlling the recirculation pump to regulate a flow rate of the recirculation pump to bring the measured filter outlet blood temperature to a preset blood temperature and maintain the measured filter outlet blood temperature at the preset blood temperature,
  (iii) Ultrafilter blood by causing plasma water to be removed from blood in the extracorporeal blood circuit through the blood treatment device, and
  (iv) Cause excess fluid to be discharged through the evacuation line.

17. The apparatus of claim 16, further comprising an air trapping device operating on the blood return line, wherein the at least one temperature sensor is positioned upstream from the air trapping device.

18. The apparatus of claim 16, further comprising a post infusion line connected to the blood return line upstream from the air trapping device, wherein the at least one temperature sensor is placed downstream from the post infusion line between the post infusion line and the air trapping device.

19. An extracorporeal blood treatment apparatus, comprising:
- a blood treatment device comprising a blood chamber and a fluid chamber separated by a semipermeable membrane;
- an extracorporeal blood circuit comprising a blood withdrawal line connected to an inlet port of the blood chamber and a blood return line connected to an outlet port of the blood chamber;
- a blood pump operable with the blood withdrawal line;
- a closed fluid line connected to an inlet port of the fluid chamber and to an outlet port of the fluid chamber, wherein the closed fluid line together with the fluid chamber form a recirculation loop;
- an evacuation line departing from the closed fluid line;
- a warming device coupled to the closed fluid line;
- a recirculation pump operable with the closed fluid line;
- at least one temperature sensor operable with the extracorporeal blood circuit to sense a blood temperature;
- at least one of: (i) a pre-infusion line connected to the blood withdrawal line, (ii) a post- infusion line connected to the blood return line, (iii) a pre-pump infusion line connected to the blood withdrawal line upstream of the blood pump, wherein the post-infusion line is connected between the outlet port of the blood chamber and the at least one temperature sensor;
- a control unit operably connected to the warming device, the recirculation pump, and the at least one temperature sensor, the control unit configured to:
  (i) receive, from the at least one temperature sensor, a signal correlated to the blood temperature defining a measured blood temperature, and
  (ii) adjust said blood temperature by controlling the warming device to regulate a fluid temperature in the recirculation loop to bring the measured blood temperature to a preset blood temperature and maintain the measured blood temperature at the preset blood temperature,
wherein the apparatus further comprises a heat exchanger located along the closed fluid line, and wherein the at least one of (ii) the post-infusion line, (i) the pre-infusion line, and (iii) the pre-pump infusion line passes through said heat exchanger to exchange heat with a fluid in the closed fluid line before reaching the extracorporeal blood circuit.

20. The apparatus of claim 19, wherein the heat exchanger is located downstream from the warming device.

* * * * *